United States Patent
Yoshitomi et al.

(10) Patent No.: US 10,877,524 B2
(45) Date of Patent: Dec. 29, 2020

(54) INFORMATION PROCESSING APPARATUS AND INFORMATION PROCESSING METHOD

(71) Applicant: SONY CORPORATION, Tokyo (JP)

(72) Inventors: Kosuke Yoshitomi, Kanagawa (JP); Jun Kimura, Kanagawa (JP); Tsubasa Tsukahara, Tokyo (JP); Ikuo Yamano, Tokyo (JP); Kei Takahashi, Tokyo (JP); Ayumi Kato, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/086,384

(22) PCT Filed: Feb. 3, 2017

(86) PCT No.: PCT/JP2017/004043
§ 371 (c)(1),
(2) Date: Sep. 19, 2018

(87) PCT Pub. No.: WO2017/169112
PCT Pub. Date: Oct. 5, 2017

(65) Prior Publication Data
US 2019/0101958 A1 Apr. 4, 2019

(30) Foreign Application Priority Data
Mar. 28, 2016 (JP) .................. 2016-063042

(51) Int. Cl.
*G06F 1/16* (2006.01)
*G04G 21/02* (2010.01)
(Continued)

(52) U.S. Cl.
CPC .......... *G06F 1/1675* (2013.01); *A61B 5/6801* (2013.01); *A61B 5/6802* (2013.01);
(Continued)

(58) Field of Classification Search
CPC ....................................... G06F 1/163
See application file for complete search history.

(56) References Cited

U.S. PATENT DOCUMENTS 5,526,208 A * 6/1996 Hatch .................. G11B 5/4846
360/294.1
6,833,656 B2 * 12/2004 Hooley .................. H04R 17/00
310/328
(Continued)

FOREIGN PATENT DOCUMENTS

CN 1525194 A 9/2004
CN 105555194 A 5/2016
(Continued)

OTHER PUBLICATIONS

International Search Report and Written Opinion of PCT Application No. PCT/JP2017/004043, dated Apr. 25, 2017, 10 pages of ISRWO.

*Primary Examiner* — Adrian S Wilson
(74) *Attorney, Agent, or Firm* — Chip Law Group

(57) ABSTRACT

For attaining the object described above, an information processing apparatus according to an embodiment of the present technology includes an acquisition unit and a generation unit. The acquisition unit acquires information related to a notification to a user. The generation unit generates control information for changing an outer shape of a wearable device on a basis of the information.

15 Claims, 8 Drawing Sheets

(51) Int. Cl.
  *G04G 21/00* (2010.01)
  *A61B 5/00* (2006.01)
  *G04G 17/02* (2006.01)
  *H04M 1/725* (2006.01)
  *A61B 5/145* (2006.01)
  *A61B 5/01* (2006.01)
  *A61B 5/024* (2006.01)

(52) U.S. Cl.
  CPC ............ *G04G 17/02* (2013.01); *G04G 21/00* (2013.01); *G04G 21/02* (2013.01); *G04G 21/025* (2013.01); *G06F 1/16* (2013.01); *G06F 1/163* (2013.01); *H04M 1/7253* (2013.01); *A61B 5/01* (2013.01); *A61B 5/02438* (2013.01); *A61B 5/14517* (2013.01)

(56) References Cited

U.S. PATENT DOCUMENTS

| | | | | |
|---|---|---|---|---|
| 7,252,313 | B2* | 8/2007 | Browne | B29C 33/308 293/128 |
| 8,568,189 | B2* | 10/2013 | Garbos | A63H 3/28 446/175 |
| 9,020,571 | B2* | 4/2015 | Chi | H04B 1/38 455/575.1 |
| 9,116,546 | B2* | 8/2015 | Birnbaum | G08B 6/00 |
| 9,510,470 | B2* | 11/2016 | Huitema | G06F 1/1652 |
| 9,560,751 | B2* | 1/2017 | Huitema | H05K 1/028 |
| 9,848,494 | B2* | 12/2017 | Huitema | G06F 1/163 |
| D819,020 | S* | 5/2018 | Choi | D14/341 |
| 10,206,623 | B2* | 2/2019 | Harrison-Noonan | A61B 5/6843 |
| 10,285,645 | B2* | 5/2019 | Bushnell | A61B 5/6843 |
| 10,289,163 | B2* | 5/2019 | Huitema | G06F 1/163 |
| 2003/0181116 | A1* | 9/2003 | Van Heerden | G06F 3/016 442/182 |
| 2004/0179431 | A1 | 9/2004 | Nakajima | |
| 2004/0239624 | A1* | 12/2004 | Ramian | G06F 3/016 345/156 |
| 2004/0261411 | A1* | 12/2004 | MacGregor | F03G 7/065 60/527 |
| 2006/0209218 | A1* | 9/2006 | Lee | G04G 9/00 349/1 |
| 2007/0132551 | A1* | 6/2007 | Mozer | E05B 47/0009 340/5.52 |
| 2008/0024963 | A1* | 1/2008 | Weksler | G06F 1/1616 361/679.01 |
| 2009/0250267 | A1* | 10/2009 | Heubel | G06F 3/016 178/18.03 |
| 2010/0253525 | A1* | 10/2010 | Engel | G08B 6/00 340/573.1 |
| 2010/0283731 | A1* | 11/2010 | Grant | G06F 3/016 345/158 |
| 2011/0102162 | A1* | 5/2011 | Gregorio | G06F 3/016 340/407.2 |
| 2011/0121953 | A1* | 5/2011 | Grant | A63F 13/245 340/407.1 |
| 2011/0188189 | A1* | 8/2011 | Park | G05B 11/01 361/679.05 |
| 2011/0234502 | A1* | 9/2011 | Yun | G06F 3/016 345/173 |
| 2012/0017702 | A1* | 1/2012 | Kawabe | G06F 3/0414 73/862.381 |
| 2014/0307369 | A1* | 10/2014 | Lee | H04M 1/0216 361/679.01 |
| 2015/0091711 | A1* | 4/2015 | Kosonen | G08B 6/00 340/407.1 |
| 2015/0185764 | A1* | 7/2015 | Magi | G06F 1/163 361/679.03 |
| 2015/0185944 | A1* | 7/2015 | Magi | G06F 1/1652 345/174 |
| 2016/0255944 | A1* | 9/2016 | Baranski | A44C 5/0069 |
| 2017/0014068 | A1 | 1/2017 | Gotoh et al. | |

FOREIGN PATENT DOCUMENTS

| | | |
|---|---|---|
| EP | 1452933 A2 | 9/2004 |
| JP | 09-224074 A | 8/1997 |
| JP | 2004-257797 A | 9/2004 |
| JP | 2013-183368 A | 9/2013 |
| JP | 2015-058308 A | 3/2015 |
| WO | 2015/041302 A1 | 3/2015 |
| WO | 2015/099957 A1 | 7/2015 |

\* cited by examiner

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2017/004043 filed on Feb. 3, 2017, which claims priority benefit of Japanese Patent Application No. JP 2016-063042 filed in the Japan Patent Office on Mar. 28, 2016. Each of the above-referenced applications is hereby incorporated herein by reference in its entirety.

TECHNICAL FIELD

The present technology relates to an information processing apparatus, an information processing method, and a program that are applicable to a wearable device.

BACKGROUND ART

From the past, various wearable devices of a glasses type, a wristwatch type, and the like have been used. By wearing a wearable device, various operations, data processing, and the like including voice calls, transmission/reception of mails, utilization of network services, and the like become possible, for example.

Patent Literature 1 discloses an incoming call indicating device that is worn on an arm like a wristwatch and used. In this incoming call indicating device, an incoming call of a cellular phone is notified by a vibrator function that has been used from the past, generation of a minute current, or display via a liquid crystal display panel or the like (paragraphs [0017] and [0020] in specification, FIGS. 3A, 3B, 3C, 3D, and 4, etc. of Patent Literature 1).

CITATION LIST

Patent Literature

Patent Literature 1: Japanese Patent Application Laid-open No. Hei 9-224074

DISCLOSURE OF INVENTION

Technical Problem

It is considered that, in the future, wearable devices will be widely used and various computer functions will be provided therein. Accompanying this, there is a need for a technology that enables a user to efficiently check and grasp a notification regarding the notification to the user.

In view of the circumstances as described above, an object of the present technology is to provide an information processing apparatus, an information processing method, and a program with which a notification from a wearable device can be efficiently checked and grasped.

Solution to Problem

To attain the object described above, an information processing apparatus according to an embodiment of the present technology includes an acquisition unit and a generation unit.

The acquisition unit acquires information related to a notification to a user; and The generation unit generates control information for changing an outer shape of a wearable device on a basis of the information.

In this information processing apparatus, upon acquisition of the information related to the notification to the user, control information for changing the outer shape of the wearable device is generated on the basis of that information. Since the outer shape of the wearable device is changed on the basis of the control information, the user can efficiently check and grasp the notification.

The generation unit may generate control information for changing the outer shape of the wearable device into a shape corresponding to the information.

Accordingly, it becomes possible to grasp a content of notification information and the like on the basis of the changed shape.

The information processing apparatus may further include a judgment unit that judges whether to change the outer shape of the wearable device on the basis of the information.

Accordingly, it becomes possible to set information that makes the notification unnecessary and the like, and realize an efficient notification.

The generation unit may generate the control information on a basis of detection information detected by a sensor provided in the wearable device.

Accordingly, it becomes possible to set a shape change corresponding to the detection information and the like, and increase notification variations.

The sensor may include a biological sensor, and the detection information may include biological information detected by the biological sensor.

Accordingly, for example, a shape change according to a physical condition of the user or the like is realized.

The information processing apparatus may further include a judgment unit that judges whether to change the outer shape of the wearable device on the basis of the detection information.

Accordingly, it becomes possible to restrict the notification in accordance with the detection information, for example.

The information may include a notification related to a predetermined service, a notification related to an apparatus state of the information processing apparatus, or a notification related to biological information of the user.

Accordingly, it becomes possible to efficiently grasp notifications of various types of information.

The control information may include a mode of the change of the outer shape into the shape corresponding to the information.

For example, by appropriately setting the mode of the shape change, it becomes possible to reliably check the notification. It also becomes possible to grasp a content of notification information and the like by the mode of the change.

The generation unit may generate, in a case of canceling the notification to the user, cancel control information for changing the outer shape into a predetermined shape from the shape corresponding to the information.

Accordingly, it becomes possible to hold a notification shape or the like until an operation to the effect that the user has checked the notification is input, for example. Accordingly, it becomes possible to reliably check the notification.

The predetermined shape may be the outer shape of the wearable device in a basic state.

Accordingly, in the next notification, the shape is deformed from the outer shape in the basic state, and thus the notification can be checked with ease.

The information processing apparatus may be integrated with the wearable device. In this case, the wearable device may include a holding function for holding the outer shape in the shape corresponding to the information.

Accordingly, electric power for holding the notification shape becomes unnecessary, and electric power consumption can be suppressed.

The information processing apparatus may further include a judgment unit that judges whether to change the outer shape of the wearable device on a basis of information related to a usage state of the information processing apparatus.

Accordingly, it becomes possible to notify the information according to the usage state.

The generation unit may set the shape corresponding to the information on a basis of information related to a usage state of the information processing apparatus.

Accordingly, the change of the outer shape corresponding to the usage state is realized.

The generation unit may generate the control information for changing at least a part of a portion of the wearable device that comes into contact with the user.

Accordingly, it becomes possible to reliably check and grasp the notification.

The information processing apparatus may further include a judgment unit that judges that it is necessary to change the outer shape of the wearable device in a case where a predetermined movement is made by the user wearing the wearable device.

Accordingly, the notification of information corresponding to a gesture of the user is realized.

The information processing apparatus may further include an execution unit that executes predetermined processing in a case where the user changes the outer shape into another shape from the shape corresponding to the information.

Accordingly, by changing the outer shape of the wearable device, it becomes possible to input a fact that the notification has been checked, execute predetermined processing related to the notified information, and the like, for example.

An information processing method according to an embodiment of the present technology is an information processing method executed by a computer system, the method including acquiring information related to a notification to a user.

Control information for changing an outer shape of a wearable device is generated on a basis of the information.

A program according to an embodiment of the present technology causes a computer system to execute the following steps.

The step of acquiring information related to a notification to a user.

The step of generating control information for changing an outer shape of a wearable device on a basis of the information.

Advantageous Effects of Invention

As described above, according to the present technology, notifications from a wearable device can be efficiently checked and grasped. It should be noted that the effects described herein are not necessarily limited, and any effect described in the present disclosure may be obtained.

MODES FOR CARRYING OUT THE INVENTION

Hereinafter, embodiments of the present technology will be described with reference to the drawings.

[Wearable apparatus]

Figure 1:
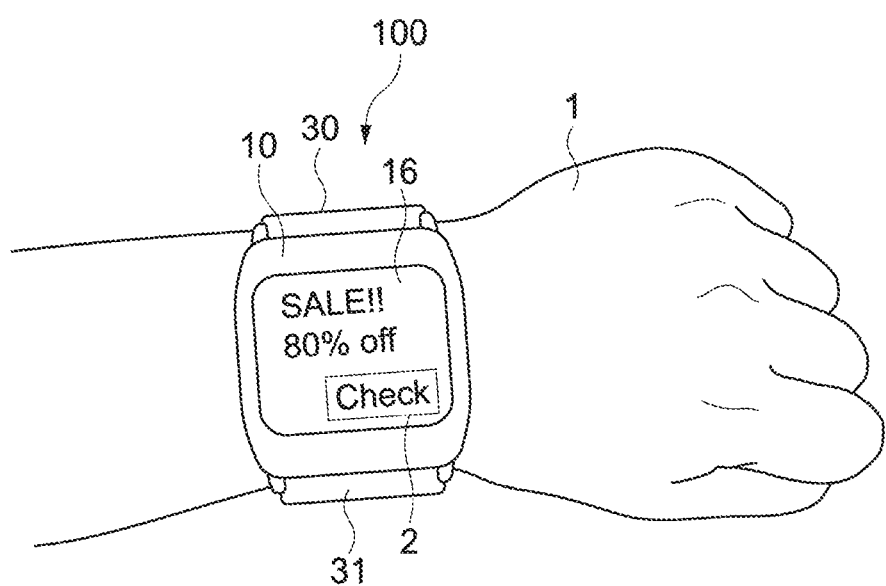
FIG. 1 A schematic diagram showing an outer appearance of a wearable apparatus according to an embodiment.

FIG. 1 is a schematic diagram showing an outer appearance of a wearable apparatus according to an embodiment of the present technology. The wearable apparatus 100 is a wristwatch-type wearable device and is used by being worn on a wrist of a user 1.

The wearable apparatus 100 includes a computer main body 10 and a band unit 30. The computer main body 10 includes various computer functions and is capable of performing various operations, data processing, and the like including voice calls, transmission/reception of mails, reproduction of audio and moving image content, utilization of network services, and the like, for example. The computer main body 10 functions as an information processing apparatus according to this embodiment.

The band unit 30 is a mechanism for enabling the user 1 to wear the apparatus on the wrist and includes an attachment band 31 that comes into contact with and holds the user 1. The attachment band 31 is connected to the computer main body 10. It should be noted that the contact with the user 1 is not limited to the case where it is brought into direct contact with a bare skin, and also includes a case where it is brought into contact via clothes and the like.

Figure 2:
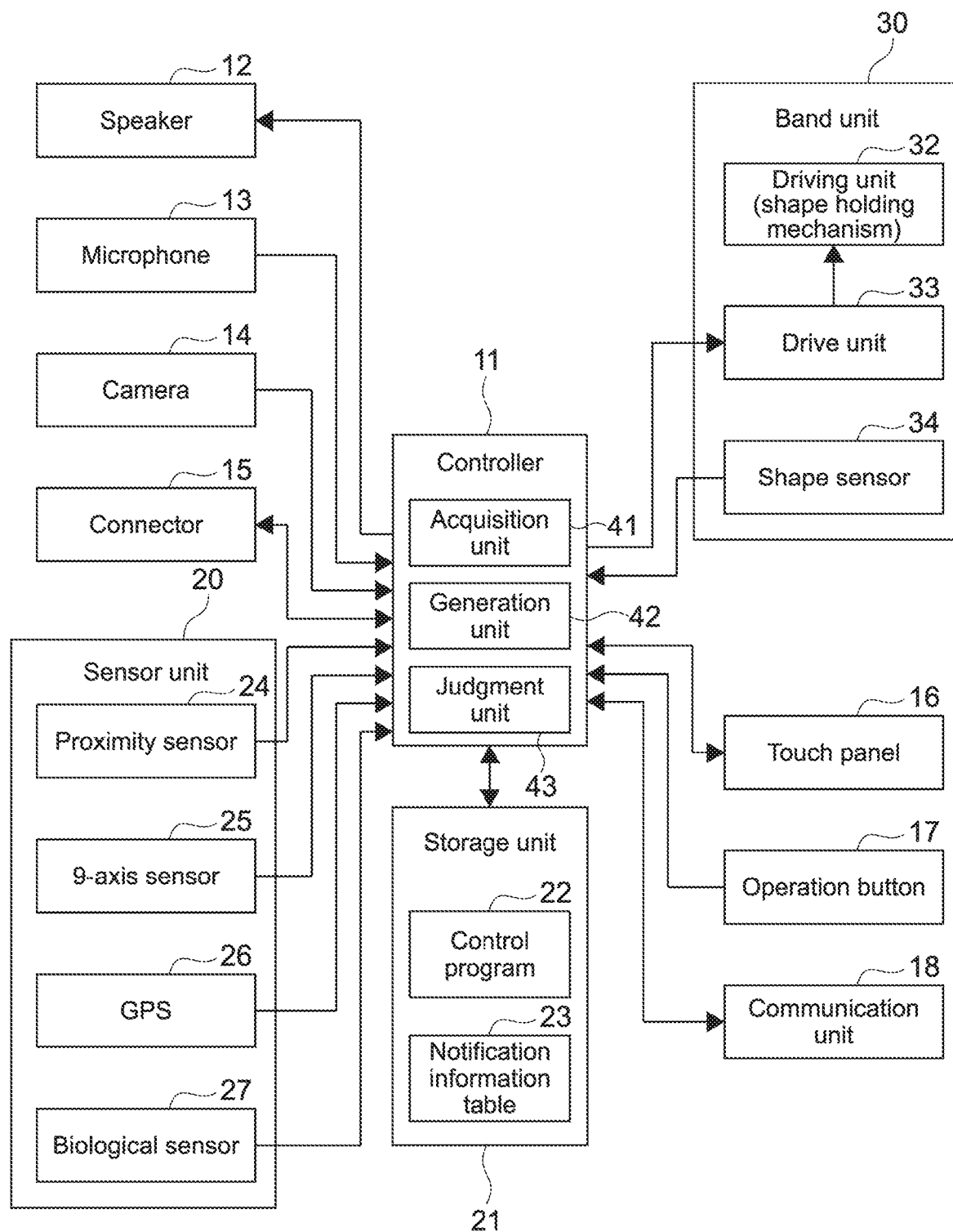
FIG. 2 A block diagram showing a functional configuration example of the wearable apparatus.

FIG. 2 is a block diagram showing a functional configuration example of the wearable apparatus 100. The wearable apparatus 100 includes a controller 11, a speaker 12, a microphone 13, a camera 14, a connector 15, a touch panel 16, an operation button 17, and a communication unit 18. The wearable apparatus 100 also includes a sensor unit 20, a storage unit 21, and the band unit 30.

The speaker 12 and the microphone 13 enable calls with other users, outputs of audio guidance and alarm sounds, reproduction of music content, inputs of instructions by audio, and the like. By the camera 14, it becomes possible to capture images of a face of the user 1 himself/herself, surrounding sceneries, and the like.

The connector 15 is a terminal for connecting with other devices. Terminals for USB (Universal Serial Bus), HDMI (registered trademark) (High-Definition Multimedia Interface), and the like are provided, for example. Further, during charging, a charge terminal of a charge dog (cradle) and the connector 15 are connected so as to perform charging.

Various images and GUIs (Graphical User Interfaces) are displayed on the touch panel 16. The user 1 can input predetermined instructions and the like by touch-operating the touch panel 16. For example, as shown in FIG. 1, sale information and the like transmitted from a web service on a network are displayed on the touch panel 16. When the user 1 who has checked the information touches a check button 2, an image on the touch panel 16 is switched.

The operation button 17 is provided for performing an operation different from operations made via the touch panel 16, such as an operation of turning on/off power supply, for example.

The communication unit 18 is a module for executing network communication, short-distance wireless communication, and the like with other devices. For example, a wireless LAN module such as WiFi and a communication module such as Bluetooth (registered trademark) are provided.

The sensor unit 20 includes a proximity sensor 24, a 9-axis sensor 25, a GPS 26, and a biological sensor 27. The proximity sensor 24 is provided on an inner circumferential side of the attachment band 10, and a detection result thereof is used for judging whether or not the wearable apparatus 100 is worn, for example. The 9-axis sensor 25 includes a triaxial acceleration sensor, a triaxial gyro sensor, and a triaxial compass sensor. The 9-axis sensor 25 is capable of detecting accelerations, angular velocities, and orientations of the wearable apparatus 100 along three axes, for example. The GPS 26 acquires information on a current position of the wearable apparatus 100.

The biological sensor 27 acquires biological information of the user 1. For example, as the biological sensor 27, a temperature sensor capable of measuring a body temperature, a heartbeat sensor capable of measuring a heart rate, a perspiration sensor capable of measuring a perspiration amount, and the like are provided.

The types of sensors to be provided as the sensor unit 20 are not limited, and an arbitrary sensor may be provided. For example, a temperature sensor, a humidity sensor, and the like that are capable of measuring a temperature, humidity, and the like of an environment where the wearable apparatus 100 is used may be provided. Various types of information detected by the sensor unit 20 correspond to detection information detected by a sensor provided in a wearable device in this embodiment.

The storage unit 21 is a nonvolatile storage device, and an HDD (Hard Disk Drive) or the like is used, for example. The storage unit 21 stores a control program 22 for controlling an overall operation of the wearable apparatus 100. The storage unit 21 also stores a notification information table 23. The notification information table 23 is a table in which notification information notified to the user 1 and an outer shape change of the attachment band 31 are associated with each other. A method of installing the control program 22 and the notification information table 23 in the wearable apparatus 100 is not limited.

The band unit 30 includes the attachment band 31 described above, a driving unit 32, a drive unit 33, and a shape sensor 34. The driving unit 32 changes an outer shape of the attachment band 31. Further, the driving unit 32 includes a shape holding mechanism for holding the outer shape of the attachment band 31. The drive unit 33 controls an operation of the driving unit 32 on the basis of control information output from the controller 11. The shape sensor 34 detects the outer shape of the attachment band 31.

FIGS. 3A, 3B, 3C, and 3D are schematic diagrams for explaining modified examples of the outer shape of the attachment band 31. FIGS. 3A, 3B, 3C, and 3D show an outer shape F0 in a basic state before deformation, and is typically a shape of the wearable apparatus 100 during normal use. In this embodiment, a shape in which the attachment band 31 becomes annular is the outer shape F0 in the basic state. An area R surrounded by the attachment band 31 becomes substantially circular, and the wrist is inserted thereinto. The outer shape F0 in the basic state may be set arbitrarily.

Figure 3A:
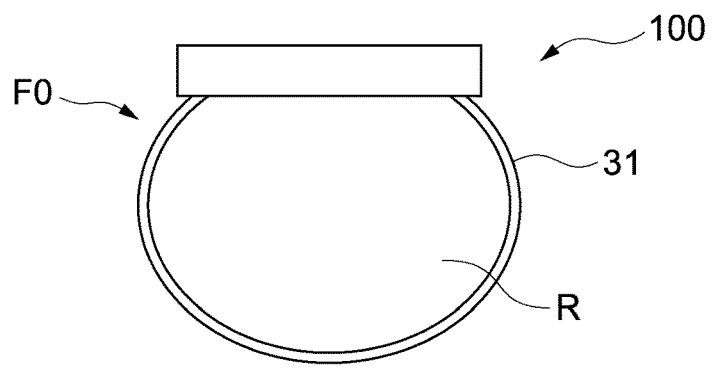
FIGS. 3A, 3B, 3C, and 3D Schematic diagrams for explaining an example of a change of an outer shape of an attachment band.
Figure 3B:
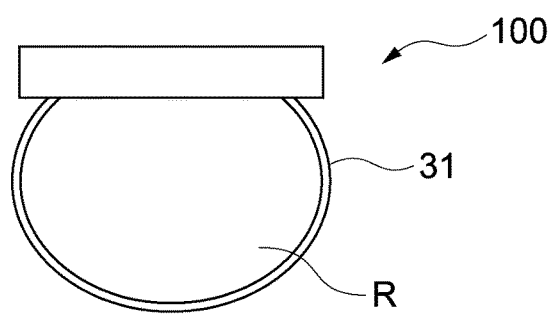

In FIG. 3B, the outer shape F0 in the basic state is deformed so that an inner diameter of the attachment band 31 becomes small. The attachment band 31 contracts, and the area R that comes into contact with the wrist becomes small. By controlling a contraction amount of the attachment band 31, that is, the area of the area R, a holding force (pressure) applied to the wrist can be controlled. When the holding force with respect to the wrist changes, a sense (tactile sense) that the user 1 gets from the wrist also changes.

Figure 3C:
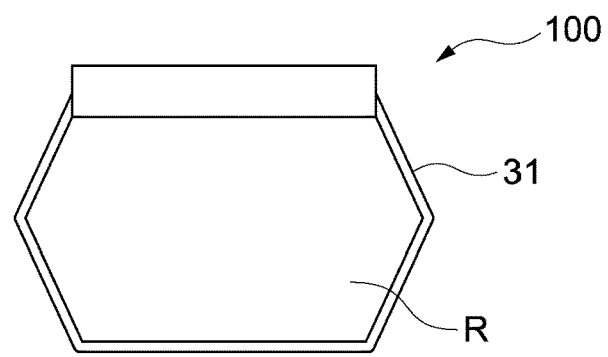

In FIG. 3C, the outer shape of the attachment band 31 is changed into a substantially hexagonal shape. In this way, the outer shape may be changed so that the area R in the attachment band 31 becomes a polygonal shape. The attachment band 31 can be deformed into not only a hexagon but also a polygonal shape having an arbitrary number of apexes equal to or larger than that of a triangle. When the outer shape of the attachment band 31 has a polygonal shape, a sense on the wrist also changes.

Figure 3D:
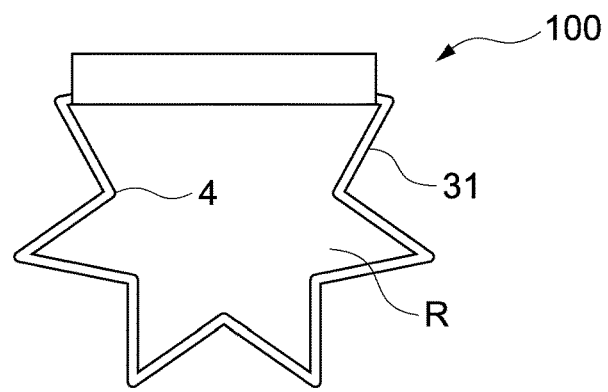

In FIG. 3D, the outer shape of the attachment band 31 is changed into a substantially star shape. Then, since the wrist of the user 1 is strongly pressed by inner apexes 4, it is possible to surely notice the change in the outer shape. In this way, the outer shape of the attachment band 31 can be deformed arbitrarily.

It should be noted that the outer shape of the attachment band 31 corresponds to an outer shape of the wearable device in this embodiment. Further, the outer shape change of the attachment band 31 is executed to such a degree that a sense (tactile sense) on a part where the wearable apparatus 100 is worn changes. Typically, the outer shape of the attachment band 31 is changed to such a degree that is visually recognizable by the user 1, though of course is not limited thereto.

FIGS. 4, 5A, 5B, and 5C are schematic diagrams showing configuration examples of the driving unit 32 that causes the attachment band 31 to be deformed. The band unit 30 shown in a cross-sectional diagram of FIG. 4 includes the attachment band 31, a plastic deformation member 35, and first and second shape-memory alloys (SMA) 36 and 37. The first and second SMAs 36 and 37 function as the driving unit 32, and the plastic deformation member 35 functions as the shape holding mechanism.

The attachment band 31 has flexibility and is formed of, for example, rubber, plastic, or the like. Both end portions 31a and 31b of the attachment band 31 are connected to the computer main body 10 so as to become annular. The computer main body 10 may be connected to an annular attachment band.

The plastic deformation member 35 is provided inside the attachment band 31 across an entire area from the end portion 31a to end portion 31b of the attachment band 31. The plastic deformation member 35 is provided at substantially a center position of the attachment band 31 in a thickness direction. As the plastic deformation member 35, a plate formed of a metal material such as aluminum and copper is used, for example. Other materials may also be used.

Figure 4:
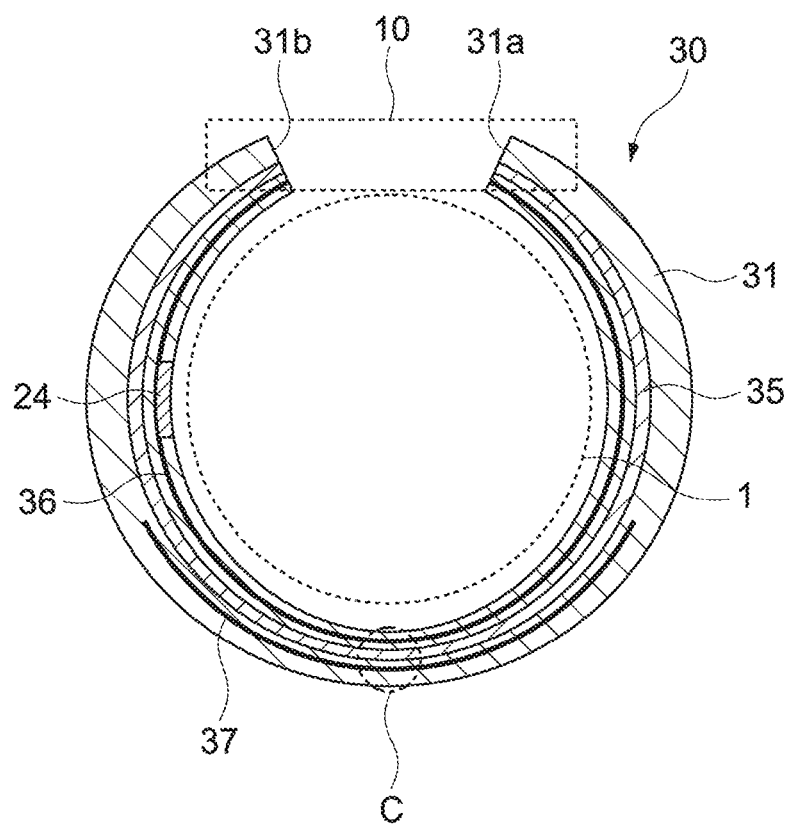
FIG. 4 A schematic diagram showing a configuration example of a driving unit that causes the attachment band to be deformed.

The first and second SMAs 36 and 37 have characteristics of contracting when applied with electric power. The contracted shape is held while the application of electric power is continued and returns to its original shape when the application stops. As shown in FIG. 4, the first SMA 36 is provided inside the attachment band 31 across the entire area from the end portion 31a to the end portion 31b. Further, the first SMA 36 is provided on an inner side of the plastic deformation member 35.

With a direction from the end portion 31a to the end portion 31b being a length direction, the second SMA 36 is provided inside the attachment band 31 at substantially a center position thereof in the length direction while having a shorter length than the attachment band 31. As shown in FIG. 4, with a center portion C of the attachment band 31 in the length direction being a center, the length of the second SMA 37 is ⅓ the length of the first SMA 36. Further, the second SMA 37 is provided on an outer side of the plastic deformation member 35. Therefore, the plastic deformation member 35 is sandwiched between the first and second SMAs 36 and 37. Specific materials and the like of the first and second SMAs 36 and 37 are not limited.

It should be noted that the proximity sensor 24 is provided at a position more on an inner side than the first SMA 36 in the vicinity of the end portion 31b of the attachment band 31. The position of the proximity sensor 24 is not limited as long as it is capable of detecting the wrist of the user 1.

Electric power is applied to the first SMA 36 by the drive unit 33 on the basis of control information from the controller 11. As a result, the first SMA 36 contracts, and the entire attachment band 31 contracts. Consequently, the outer shape of the attachment band 31 can be changed into the outer shape as shown in FIG. 3B.

Since the plastic deformation member 35 is provided in this embodiment, even if the application of electric power to the first SMA 36 is stopped, the shape of the attachment band 31 is held and does not return to its original shape. Therefore, the shape of the attachment band 31 is held in a state where the attachment band 31 is contracted. Therefore, it becomes possible to hold the deformation of the attachment band 31 without requiring electric power and thus suppress electric power consumption.

When electric power is applied to the second SMA 37, due to the contraction of the second SMA 37, the entire attachment band 31 is released with the center portion C of the attachment band 31 being a reference. Therefore, it becomes possible to cause the shape to return from the outer shape shown in FIG. 3B to the outer shape F0 in the basic state shown in FIG. 3A.

By controlling the application of electric power to the first and second SMAs 36 and 37 in this way, the contraction and release of the attachment band 31 can be controlled with ease. It should be noted that a material, size, and the like of the plastic deformation member 35 are set as appropriate in accordance with a contraction force and restoration force of each of the first and second SMAs 36 and 36.

Figure 5A:
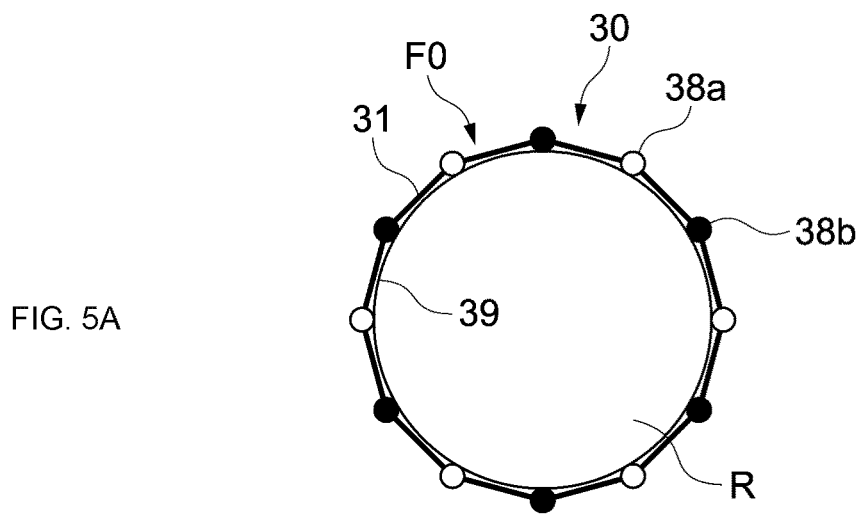
FIGS. 5A, 5B, and 5C Schematic diagrams showing configuration examples of the driving unit that causes the attachment band to be deformed.
Figure 5B:
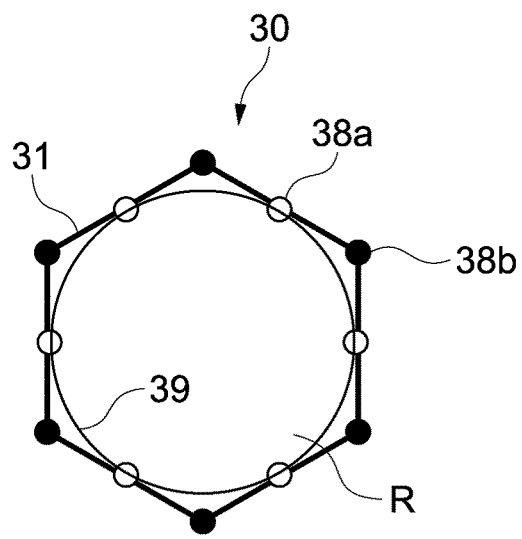
Figure 5C:
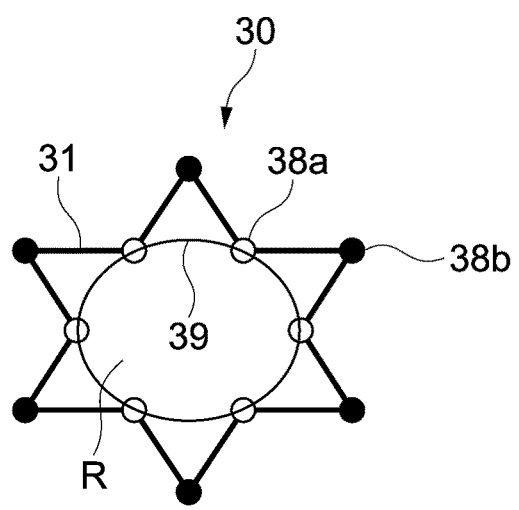

The band unit 30 shown in FIGS. 5A, 5B, and 5C includes the attachment band 31, first and second joint portions 38a and 38b, and a wire 39. The first and second joint portions 38a and 38b are provided alternately at substantially equal intervals with respect to the attachment band 31. The first joint portion 38a is movable both outwardly and inwardly with respect to the center of the area R of the attachment band 31. The second joint portion 38b is movable only inwardly.

Further, the first and second joint portions 38a and 38b are biased from the center toward the outside by a spring (not shown) or the like so as to become the outer shape F0 in the basic state shown in FIG. 5A. The wire 39 is connected only to the first joint portion 38a.

A motor 33 and the like are controlled by the drive unit 33 on the basis of the control information from the controller 11, and the wire 39 is wound. As a result, the outer shape of the attachment band 31 is changed from the outer shape F0 shown in FIG. 5A to the substantially hexagonal shape shown in FIG. 5B and the star shape shown in FIG. 5C. By stopping the motor or the like while the wire 39 is wound up and fixing the wire 39, the shape of the attachment band 31 can be held. When the wire 39 is reeled out, it becomes possible to cause the attachment band 31 to return to the outer shape F0 in the basic state by a bias force applied to the first and second joint portions 38a and 38b toward the outer side.

Specific configurations of the driving unit 32 and the shape holding mechanism are not limited, and arbitrary configurations may be used. Further, an arbitrary technology may be used for changing the outer shape of the attachment band 31. For example, the outer shape change can be realized by making the joint portions shown in FIGS. 5A, 5B, and 5C movable by using the deformations of the SMAs shown in FIG. 4 or making them movable by other actuators.

Specific configuration examples of the drive unit 33 and the shape sensor 34 are also not limited, and arbitrary configurations may be used. As the drive unit 33, for example, an IC (integrated circuit) for driving the driving unit 32 is used. As the shape sensor 34, for example, a proximity sensor, a displacement sensor, or the like is used.

The controller 11 shown in FIG. 2 controls operations of the respective block of the wearable apparatus 100. The controller 11 includes a hardware configuration requisite for a computer, such as a CPU and a memory (RAM, ROM). Various types of processing are executed by the CPU loading a control program stored in the storage unit 21 into the RAM and executing it.

As the controller 11, for example, PLD (Programmable Logic Device) such as FPGA (Field Programmable Gate Array), or other devices such as ASIC (Application Specific Integrated Circuit) may be used.

In this embodiment, the CPU of the controller 11 executes a program according to this embodiment, to thus realize an acquisition unit 41, a generation unit 42, and a judgment unit 43 as functional blocks. The acquisition unit 41 acquires information related to a notification to the user 1. The information related to the notification is typically notification information notified to the user 1. The present technology is not limited to this, and other types of information such as information to be notified to the user 1 are also included.

The generation unit 42 generates control information for changing the outer shape of the wearable apparatus 100 on the basis of the information related to the notification. The judgment unit 43 judges whether to change the outer shape of the wearable apparatus 100 on the basis of the information related to the notification. The judgment unit 43 can also be regarded as a block that judges a necessity of the notification to the user 1 by a change in the outer shape.

Therefore, in this embodiment, an information processing method according to this embodiment is executed by the controller 11. It should be noted that dedicated hardware may be used as appropriate to realize the acquisition unit 41, the generation unit 42, and the judgment unit 43.

Further, the controller 11 is capable of acquiring information related to a usage state of the wearable apparatus 100 on the basis of a detection result from the sensor unit 20. Here, the information related to the usage state includes various types of information related to a state where the wearable apparatus 100 is used. For example, information related to a state of the user 1 using the wearable apparatus 100, information related to a state of the wearable apparatus 100 to be used, information related to a usage environment where the wearable apparatus 100 is used, and the like are included.

Motion information related to a motion of the user 1 is acquired as state information of the user 1. For example, information of walking, traveling, traveling by train, driving, and the like is acquired. In addition, information related to a posture as in sitting, standing, bending forward, facing sideways, facing upwards, and the like is acquired.

Further, information related to a current position of the user 1, more specifically, whether the user is currently indoor, outdoor, in midst of a meeting, or the like, can also be acquired. Furthermore, information on whether the user is asleep or awake, and biological information such as a body temperature, a pulse rate, and a perspiration amount are also acquired. These pieces of state information of the user 1 can be acquired by an arbitrary behavior analysis technology such as a behavior analysis that uses parameters obtained by machine learning, and the like, for example.

As information of an apparatus state of the wearable apparatus 100, various types of information such as a function being executed, an operation mode, whether the apparatus is attached to the attachment target, an attachment position with respect to the user 1, a remaining battery amount, connection with the charge dock, and an apparatus temperature, are acquired. Various types of information such as a temperature, a humidity, a current position, weather, and date and time are acquired as the information on the usage environment. Sensors, devices, and the like for acquiring these pieces of information are provided in the wearable apparatus 100 as appropriate.

Further, the state information of the user 1, apparatus state information, and usage environment information may be acquired on the basis of communication with an apparatus mounted on an automobile or the like, information on a network, and the like.

[Outer Shape Change of Band Unit]

Figure 6:
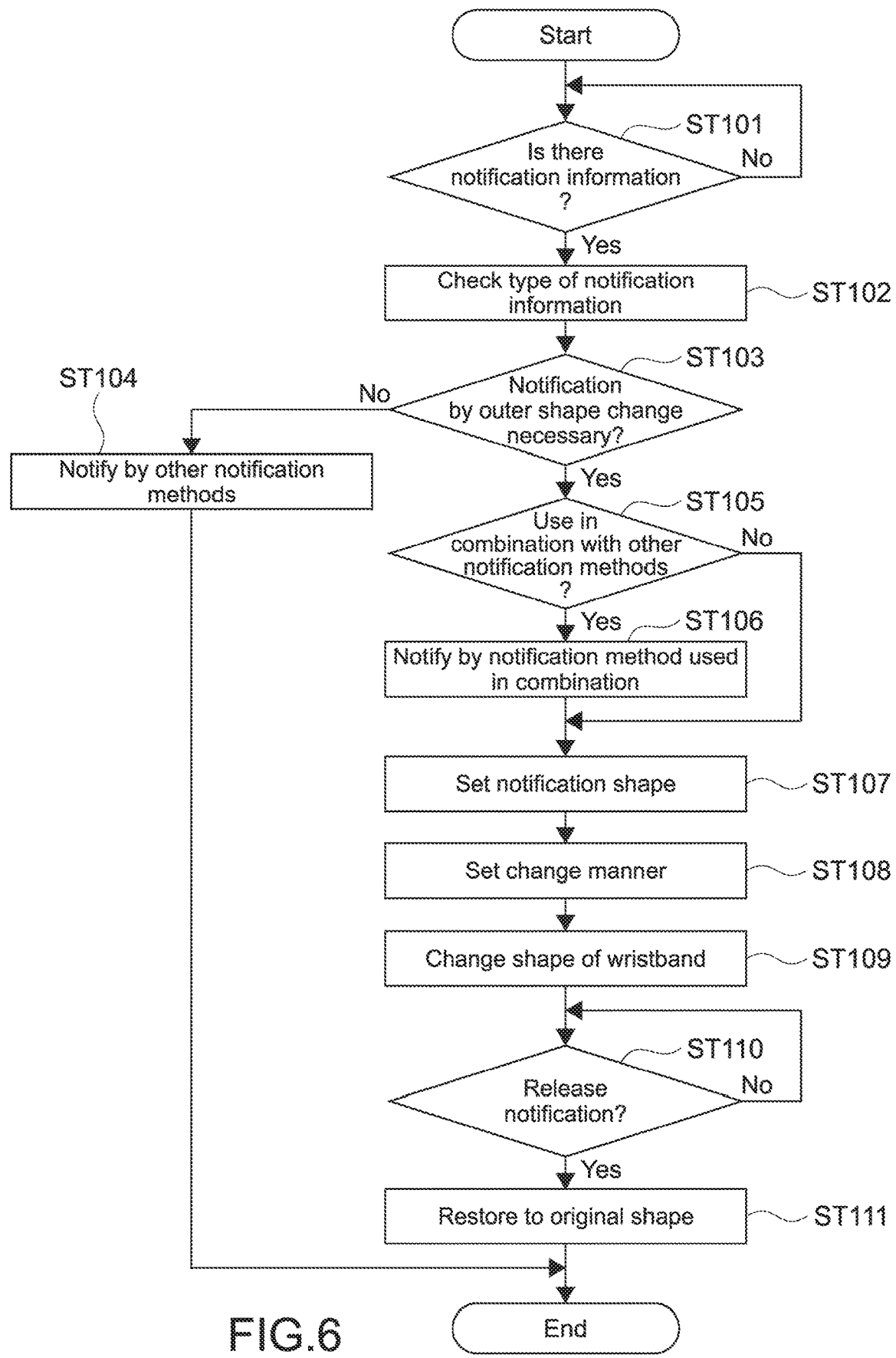
FIG. 6 A flowchart showing a processing example of a change of the outer shape of the attachment band.

FIG. 6 is a flowchart showing a processing example an outer shape change of the attachment band 31. First, presence/absence of notification information to be notified to the user is judged (Step 101). In other words, it is judged whether notification information has been acquired by the acquisition unit 41.

As the notification information, arbitrary information can be set. An example thereof includes notification information related to various services such as a communication service, network service, and application service usable by the wearable apparatus 100. For example, there is arbitrary notification information such as an incoming call, mail reception, notification from a website or the like, whether a post has been made on SNS (Social Networking Service), and the like.

Notification information related to the apparatus state of the wearable apparatus 100 is also included. For example, there is arbitrary notification information such as a start/end of a predetermined operation mode, a remaining battery amount, a charge completion, and an alarm. Notification information related to the state of user 1 is also included. For example, there is arbitrary notification information including notifications related to a movement speed, a movement amount, a current position, and the like, notifications related to biological information such as a body temperature, a pulse rate, and a perspiration amount, and the like. In addition, various types of detection information detected by the sensor unit 20 may also be set as the notification information.

For example, it is judged that notification information exists in a case where a notification as a target of a push notification, a notification in which a setting is made to be notified when a predetermined condition is satisfied, or the like occurs (Yes in Step 101). If there is no notification information, monitoring of presence/absence of notification information is continued as it is (No in Step 101).

When there is notification information, a type of the notification information is checked (Step 102), and the judgment unit 43 judges whether a notification by the outer shape change of the attachment band 31 is necessary (Step 103). The necessity of the notification by the outer shape change is typically judged on the basis of notification information (notification content).

For example, by the setting of the user 1, it is possible to set whether to perform the notification by the outer shape change with respect to each piece of arbitrary notification information including the notification information related to the services, the notification information related to the apparatus state, the notification information related to the state of the user, and the like described above. Specifically, it is possible to set notification information for which the notification by the outer shape change is desired, set notification information that does not require the notification by the outer shape change, and the like. Therefore, it is possible to customize the notification setting for each user 1.

The information on the necessity of the notification by the outer shape change is stored in the notification information table 23 stored in the storage unit 21. By referencing the notification information table 23, the controller 11 judges the necessity of the outer shape change for each piece of notification information. The present technology is not limited to the case where the judgment on the necessity of notification is executed on the basis of table information, and other methods may also be used.

The necessity of the outer shape change may be judged on the basis of the information on the user state, apparatus state, or environment state that can be acquired by the controller 11. For example, in a case where it is detected that the user is asleep or driving an automobile, it is judged that the outer shape change is unnecessary even when a flag indicating that there is a notification to be notified by the outer shape change, or the like is stored.

In this way, the necessity of the outer shape change may be judged on the basis of various types of information related to the usage state of the wearable apparatus 100. As a result, a flexible information notification according to the usage state is realized. It should be noted that processing of judging that, in a case where a flag indicating that there is a notification to be notified by the outer shape change, or the like is stored, the notification is unnecessary on the basis of other conditions and the like can also be regarded as processing that restricts notifications by other conditions.

In a case where it is judged that the notification by the outer shape change is unnecessary (No in Step 103), a notification by other means is executed (Step 104). For example, an output of a notification sound (notification message), display of a notification GUI, and the like are executed. It should be noted that a step of judging whether to execute the notification by other means may be provided.

In a case where it is judged that the notification by the outer shape change is necessary (Yes in Step 103), it is judged whether to notify the user 1 in combination with other notification methods (Step 105). In a case where other notification methods are used in combination (Yes in Step 105), the notification methods that are used in combination are executed (Step 106).

In a case where other notification methods are not used in combination (No in Step 105), a notification shape is set (Step 107). The notification shape is the outer shape of the attachment band 31 set for notifying the user 1. For example, the shapes as shown in FIGS. 3B, 3C, and 3D can be exemplified, but the present technology is not limited thereto, and an arbitrary shape may be set as the notification shape. In this embodiment, the notification shape corresponds to a shape corresponding to information related to a notification.

The notification shape is stored in the notification information table 23. By referencing the notification information table 23, the controller 11 can easily set the notification shape. Typically, the notification shape corresponding to the notification information is set for each piece of notification information. Accordingly, it is possible to grasp what kind of notification the notification is by feeling a change in a tactile sense accompanying the outer shape change or visually checking the outer shape change.

When the notification shape is set, a mode of the change to the notification shape is set (Step 108). The mode of the change includes, for example, a deformation speed, a deformation pattern, and the like. For example, whether to change the shape at once at high speed or change it slowly in the case of causing the shape to be changed from the outer shape F0 in the basic state shown in FIG. 3A to the respective notification shapes shown in FIGS. 3B, 3C, and 3D, and the like are set. Alternatively, in the case of causing the outer shape to be changed to the substantially star shape shown in FIG. 3D, a setting in which the shape is sequentially changed from the apex on the right-hand side so as to form the star shape or a setting in which the outer shape is changed in an order in which the star shape is drawn by one stroke, is also possible.

The change mode is also stored in the notification information table. It is also possible to set the same notification shape for different types of notification information by setting the change mode corresponding to the notification information, that is, by differentiating the change speed, the change pattern, and the like. The user 1 can grasp what kind of notification the notification is on the basis of the change mode.

When the notification shape and the change mode are set, the generation unit 42 generates control information for deforming the attachment band 31. The generated control information is output, and thus the shape of the attachment band (referred to as wristband in figure) is changed (Step 109).

After that, it is judged whether to cancel the notification (Step 110). The judgment on whether to cancel the notification is made on the basis of a presence/absence of an input indicating that the notification has been checked by the user 1, whether a predetermined notification time has elapsed, and the like, for example.

In a case where the notification is not canceled (No in Step 110), the outer shape of the attachment band 31 is held as it is. In a case where the notification is canceled (Yes in Step 110), cancel control information for changing the attachment band 31 from the notification shape to a non-notification shape is generated and output. The non-notification shape corresponds to a predetermined shape in this embodiment, and is typically the outer shape F0 in the basic state. Accordingly, in a case where the notification is canceled, the outer shape returns to the outer shape F0 in the basic state (Step 111). Of course, other predetermined shapes may be set as the non-notification shape.

Further, the change mode may be set in a case where the shape is caused to return from the notification shape to the outer shape F0 in the basic state. For example, return at once, return slowly, and the like are set. Alternatively, a setting in which the shape is sequentially changed from an apex on the left-hand side so as to form a circle in a case where the outer shape shown in FIG. 3D is caused to return to the outer shape F0 in the basic state, or the like is possible. Further, the change mode (restoration method) may be set in accordance with the notification information, information related the usage state, and the like.

Hereinafter, examples of the notification by the shape change according to the present technology will be described.

In a case where an importance degree parameter is associated with the notification information, the notification shape and the change mode are set in accordance with the importance degree. For example, in a case where the importance degree is high, a shape change amount is set to be large, and tightening with a strong holding force is realized. Alternatively, the attachment band 31 can be greatly loosened or the like. The user 1 can grasp a reception of an important mail, an entry for an event that the user has been interested in from before, and the like on the basis of a large change in a tactile sense and the like.

A shape change corresponding to an urgency degree of notification information may also be set. For example, a shape change amount per unit time is set to be large. As a result, a sudden shape change is made, and thus it becomes possible to grasp a reception of an urgent message or the like. It should be noted that the notification shape and the outer shape F0 in the basic state may be switched alternately at high speed. In this case, a change different from a vibration caused by a so-called vibrator function, that is, a continuous change of a shape that can sufficiently be checked visually, is executed.

It is also possible to efficiently notify that a current date and time is within a predetermined period or that a current position is within a predetermined area by the shape change. A predetermined notification shape and change mode are set so as to change the outer shape at a timing the current date and time enters a predetermined period or the current position enters the predetermined area (Steps 101 to 109 in FIG. 6). The cancel of the notification is judged at a timing the current date and time or current position comes out of a predetermined period or area, and the shape is caused to return to the outer shape F0 in the basic state (Steps 110 and 111). Accordingly, for example, a notification of a SALE period and a notification of entry/exit into/from a WiFi area become possible.

In the case of notifying a remaining amount, an elapsed time, or the like, the shape change amount can be set as appropriate in accordance with an amount to be notified. For example, a setting in which the shape of the attachment band 31 is changed stepwise into a star shape as the remaining battery amount decreases, or the like is possible. Further, in a case where the wearable apparatus 100 is being charged, a setting in which the attachment band 31 gradually returns to the outer shape F0 in the basic state as charging progresses, or the like is also possible. In this case, a plurality of notification shapes may be set as stepwise shapes.

A plurality of notification shapes or a plurality of change modes in which power consumptions due to the deformations differ may be set in accordance with the remaining battery amount. For example, in a case where the remaining battery amount is small, the notification shape and the change mode having a small power consumption, in which the deformation amount is small and the deformation progresses slowly, are set.

Furthermore, in a case of notifying a remaining time of a timer or the like, a plurality of notification shapes according to the remaining times may be set. For example, the shape change is set discretely in such a manner that a change timing is shortened. As a result, it becomes possible to shorten the shape change interval in accordance with timings at which the timer reaches 10 minutes, 5 minutes, 1 minute, and 30 seconds. Consequently, it becomes possible to sensuously grasp the remaining time and also perform countdown by the shape change.

In a case where the user 1 is sleeping, it is also possible to postpone the shape change until the time to wake up. In other words, the notification is judged as unnecessary (notification is restricted) until the user wakes up. Further, in the case where the user is driving or playing sports, it is also possible to postpone the shape change or slow the shape change so as not to disturb the drive or sports being played. It should be noted that in a case where the user wishes to reliably check the notification even while playing sports, it is also possible to largely set the shape change amount while playing sports.

In addition, while driving or playing sports, restrictions may be set so that a shape that will become a burden regarding movements in the drive and sports, a shape that will hinder the movements, a shape that is likely to come off from the body, and the like are not set as the notification shape. In other words, it is also possible to avoid a change to the shapes as described above.

In a case where it is judged that the physical condition is poor on the basis of the biological information of the user 1, it is possible to reduce the shape change amount to the notification shape or lower the change speed. Of course, it is also possible to restrict the outer shape change. In other words, the notification shape and the change mode may be set and the necessity of the outer shape change may be judged on the basis of the biological information.

In a case where the user is detected to be in midst of a meeting, in a mass transportation system, or other quiet environments, the shape change is executed so as to suppress generation of sounds. For example, the change speed is sufficiently suppressed. In addition, in a case where the wearable apparatus 100 is worn at a plurality of positions of a body, the outer shape of the wearable apparatus 100 at a position most unnoticeable from around is changed. Such a setting is also possible.

In addition, the notification shape and the change mode may be set and the necessity of the outer shape change may be judged on the basis of various types of detection information detected by the sensor unit 20.

The notification shape and the change mode may be set to be differentiated in accordance with whether the wearable apparatus 100 is being worn or not. For example, in a case where the wearable apparatus 100 is not worn by the user 1, there is no need to consider the burden on the body, so the shape change amount is set to be large. As a result, since the outer shape can be changed so that it becomes significantly conspicuous in a visual sense, it becomes possible to reliably grasp the notification. In other words, according to the present technology, it becomes possible to check the notification even in a case where the wearable apparatus 100 is not worn.

As described above, in the wearable apparatus 100 according to this embodiment, when information related to a notification to the user 1 is acquired, control information for changing the outer shape of the attachment band 31 is generated on the basis of that notification information. Since the outer shape of the attachment band 31 changes on the basis of the control information, the user 1 can efficiently check and grasp the notification.

Whether to make the notification by the outer shape change and to what shape and in what mode the outer shape is to be changed can be dynamically set on the basis of information on a content of the notification information, the user state, the apparatus state, and the like. Therefore, it is possible to realize extremely large variations in the notification.

Further, since the notification shape is held until the notification is canceled, a continuous notification is realized. For example, even in a case where the user forgets about the notification, the user can remember the notification by recognizing the change in the outer shape afterwards. Furthermore, even in a case where the user does not notice the notification itself (i.e., change of outer shape itself), the user can easily notice that there has been a notification by recognizing the change in the outer shape by a tactile or visual sense.

It should be noted that electric power may be used for holding the shape. Even in this case, the continuous notification can be realized.

Due to prevalence of networks constantly connectable with mobile apparatuses, various notification services have come to use. Prevalence of wearable apparatuses is expected from now on, and it is considered that new notification services that provide notifications based on behaviors and biological information of users, and the like will appear and opportunities to use such notifications will increase.

Audio, vibrations, an LED (light-on/blink), and a GUI can be used as notification means. In the notification that uses audio, there are problems that there are cases where the notification is not noticed at noisy places or the notification cannot be used in public places, a user gets confused when there are people who have set the same notification sound, and the like.

In the notification that uses vibrations, there is a problem that it is difficult to notice the notification while making a body motion such as during an exercise. In the notification that uses LED or GUI display, the notification may be overlooked when not paying attention to the LED or a screen. In addition, in a case where an operation of the apparatus is not input, the display of the GUI is often stopped, and there is a high possibility that the notification will not be noticed.

In the notification method based on the outer shape change according to this embodiment, the notification can be notified by changing the tactile sense with respect to the user 1 in any environment. Moreover, by making a large deformation equal to or larger than the vibration, it becomes possible to sufficiently check the notification. Further, by holding the shape, it is possible to surely check the notification. Furthermore, in a case where the user is working while concentrating or the like, it is possible to prevent the notification from hindering a behavior of the user. In addition, an action of viewing the screen to check the notification and an action of stopping the notification sound become unnecessary, and extremely high operability can be exerted.

Other Embodiments

The present technology is not limited to the embodiment described above, and various other embodiments can be realized.

Figure 7A:
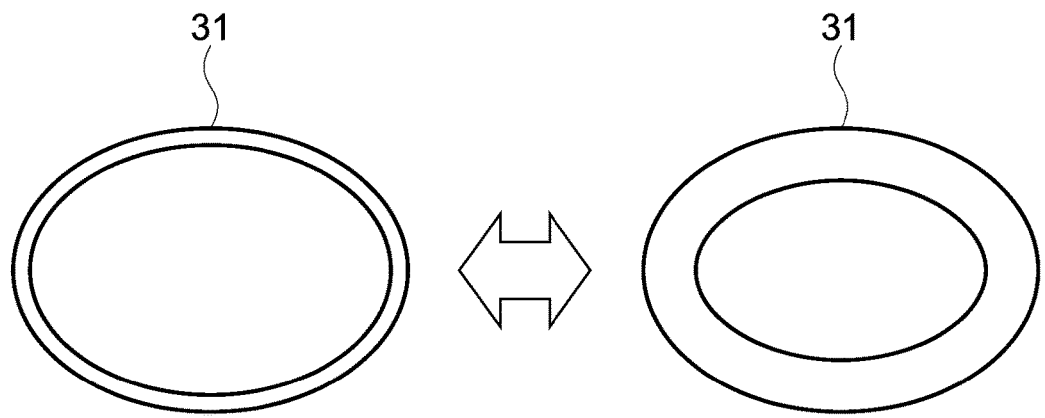
FIGS. 7A, 7B, and 7C Schematic diagrams showing other configuration examples of the driving unit.
Figure 7B:
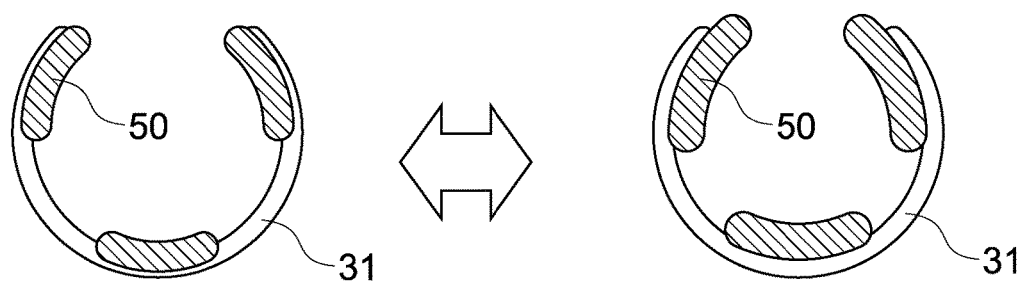
Figure 7C:
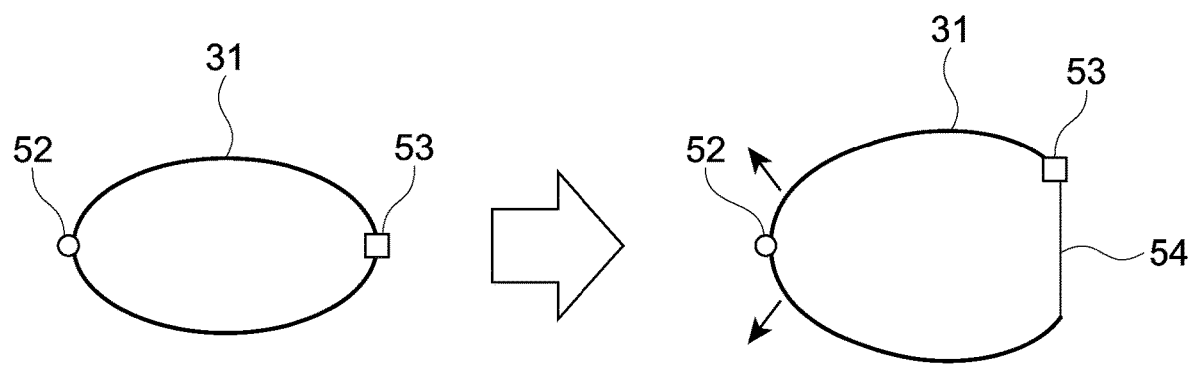

FIGS. 7A, 7B, and 7C are schematic diagrams showing other configuration examples of the driving unit. A mechanism that can be inflated by inflow of air or the like may be used as the driving unit. As shown in FIG. 7A, the attachment band 31 itself may be inflated, or an inflation member or the like may be provided inside the attachment band 31. By controlling the inflow of air or the like, it becomes possible to change the outer shape of the attachment band 31 and change the tactile sense from the attached part. It should be noted that the inflow of air or the like can be executed by a pump or the like.

As shown in FIG. 7C, the attachment band 31 may include a joint portion 52 and a lock mechanism 53. In a case where it is judged that the notification is necessary, a lock of the lock mechanism 53 is released. As a result, the attachment band 31 is loosened at once, so it becomes possible to reliably grasp the notification. It should be noted that a string 54 may be provided so that the attachment band 31 does not fall off during unlocking.

Further, a bell or the like may be fixed to the attachment band 31 in a state where the bell does not ring, and the fixation of the bell or the like may be released. As a result, the notification can be checked by a change in the tactile sense and the sound of the bell. In this way, the release of the lock mechanism, the fixing mechanism, or the like may be executed as the outer shape change. Specific configurations of the lock mechanism, the fixing mechanism, and the like are not limited, and a plunger mechanism that uses an electromagnetic force, or the like is used, for example.

Figure 8:
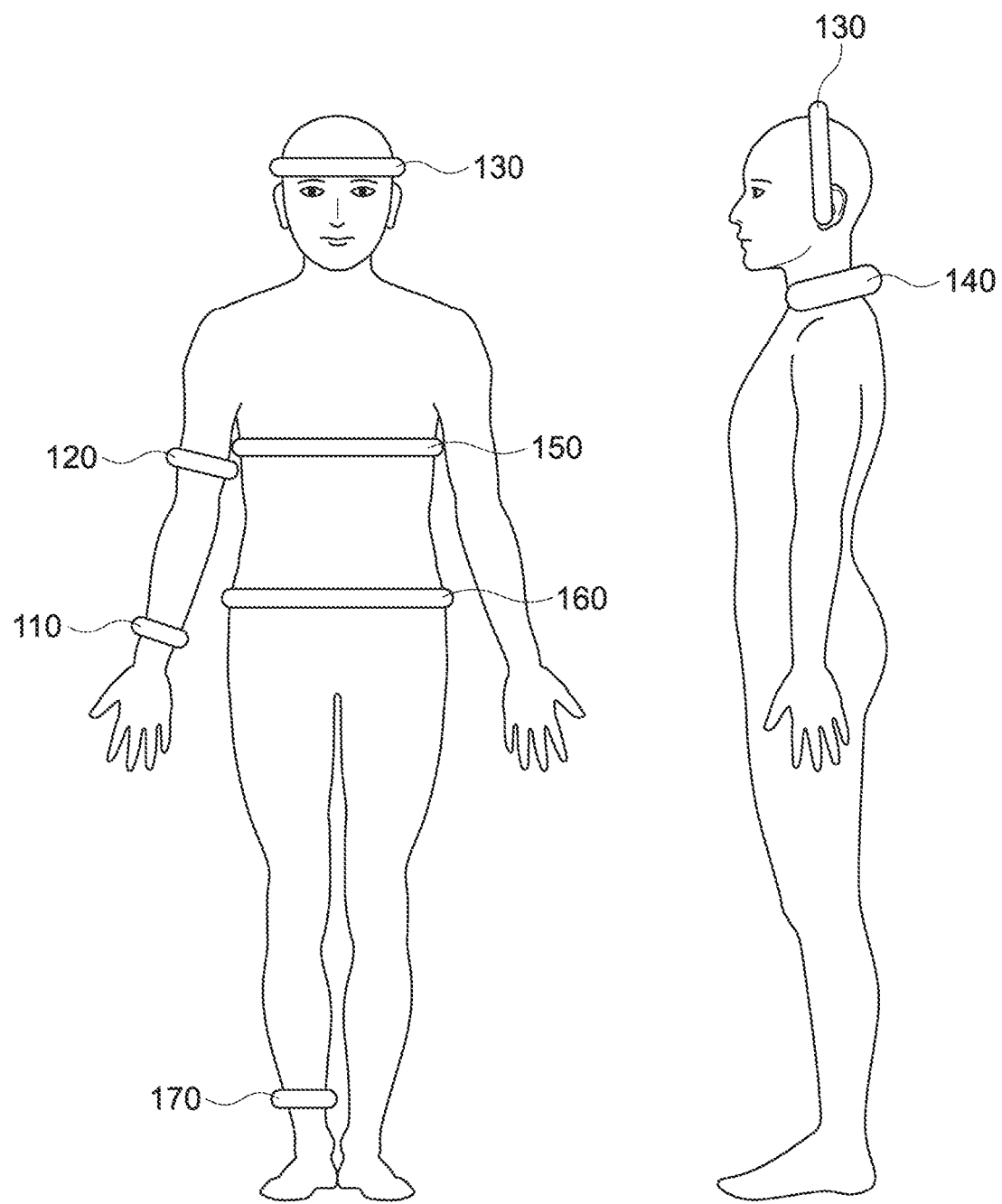
FIGS. 8 A diagram for explaining other examples of the wearable apparatus.

FIG. 8 is a diagram for explaining another example of the wearable apparatus 100. As the wearable apparatus 100, there are various forms such as a wristband-type apparatus 110 to be worn at a wrist, a bracelet-type apparatus 120 to be worn at an upper arm, a headband-type (head-mounted type) apparatus 130 to be worn on a head, a neckband-type apparatus 140 to be worn on a neck, an body-type apparatus 150 to be worn at a chest, a belt-type apparatus 160 to be worn at a waist, and an ankle-type apparatus 170 to be worn at an ankle.

Further, ring-type, necklace-type, earring-type, and pierce-type wearable apparatuses and wearable apparatuses usable in shoe soles can also be developed. The present technology is applicable to these various wearable apparatuses. For example, the notification shape and change form corresponding to an attachment position may be set as appropriate. Moreover, the necessity of the outer shape change may be judged in accordance with a setting position.

A wearable apparatus that can be used by being worn wherever the user likes among the wrist, the upper arm, the foot set, and the like is also possible. In this case, the controller may detect the attachment position so that the notification shape and change form corresponding to the attachment position are set automatically. For example, when worn on an ankle, a setting in which the shape change amount is set to become larger than that in the case of being worn on a wrist, is possible.

It may be judged that the notification is necessary in a case where the user makes a predetermined gesture (movement) in Step 103 shown in FIG. 6. For example, it may be judged that the notification is necessary in a case where a gesture of twisting a wrist on which the wearable apparatus is worn, or the like is made, and change the outer shape of the attachment band.

Specifically, the outer shape change may be executed in accordance with an intention of the user. Accordingly, for example, it becomes possible for the user who has received a notification by another notification method to change the shape in order to remember that notification. Further, the shape change can be executed with respect to a desired notification without making a setting of notification information that requires the outer shape change, or the like. It should be noted that the notification by another notification method may be canceled by the a gesture of the user.

The stop of the hold of the notification shape, that is, restoration to the outer shape in the basic state, may be executed by a gesture of the user.

Further, in a case where the outer shape is changed from the notification shape to another shape by the user, it may be regarded as an input of a predetermined operation so that predetermined processing is executed. For example, it is assumed that the outer shape of the attachment band 31 is restored from the notification shape to the outer shape in the basic state by the user. For example, a case where a star shape is manually restored to a normal annular shape, or the like is conceivable.

In this case, for example, a fact that the notification has been checked is input, or predetermined processing related to the notification information is executed. For example, processing of displaying a text of a received mail, activating a predetermined application and displaying an operation screen, or transmitting speed information, pulse information, and the like obtained during traveling to a predetermined web server may be executed. As a result, operability of the wearable apparatus can be improved.

The processing to be executed may be selected in accordance with the mode of the change of the outer shape by the user. For example, it is possible to execute first processing when restored slowly and execute second processing when restored at once. It should be noted that a block that executes the predetermined processing in accordance with the change in the outer shape by the user corresponds to an execution unit according to the present technology, and is realized by a CPU that executes a predetermined program, or the like, for example.

A plurality of pieces of notification information may occur. In this case, priority parameters may be attached to the notification information so that the judgment on the necessity of the notification by the outer shape change and the generation of control information are executed from the notification information having a high priority. Alternatively, the outer shape may be changed so as to become a notification shape having a largest change amount. Further, the biological information, apparatus state information, and the like may be referenced when selecting the notification information to be prioritized.

The method of using the notification by the outer shape change and the notification by other notification methods in combination can also be set arbitrarily. For example, audio/image and the outer shape change may be combined so that a predetermined character or the like is evoked. A case where the band unit to be worn by the user is constituted of electronic paper, a flexible display, or the like is also conceivable, and a unique deformation that leaves an impression can also be realized. As a result, the user can reliably grasp the notification.

The judgment on the necessity of the outer shape change does not need to be executed. Specifically, predetermined set control information may constantly be generated and output in a case where notification information is acquired. Accordingly, it becomes possible to simplify the processing and shorten a processing time.

In the descriptions above, the generation of control information and the judgment on the necessity of the outer shape change are executed by the controller of the wearable apparatus. Alternatively, the generation of control information and the judgment on the necessity of the outer shape change may be executed by an arbitrary computer configured separately from the wearable device.

For example, the band unit 30 shown in FIG. 2 is independent as a wearable device and is worn on the wrist of the user. Another block including the controller 11 is configured by a mobile apparatus such as a smartphone, for example, and is carried by the user. In a case where it is judged that a notification is necessary by the mobile apparatus, control information is output from the mobile apparatus to the wearable device, and the outer shape of the wearable device is changed. Even with such a configuration, it is possible to exert the effects described above.

In contrast, it can be said that the wearable apparatus 100 shown in FIG. 1 is an apparatus in which the information processing apparatus according to the present technology and the wearable device are integrated.

Furthermore, the generation of control information and the judgment on the necessity of the outer shape change can be executed not only in a computer system constituted of a single computer but also in a computer system in which a plurality of computers operate in an interlocking manner. It should be noted that in the present disclosure, the system means a group of a plurality of constituent elements (apparatuses, modules (components), etc.), and whether all constituent elements are within the same casing is irrelevant. Therefore, a plurality of apparatuses that are accommodated in separate casings and connected via a network and a single apparatus in which a plurality of modules are accommodated in a single casing are both systems.

Execution of the information processing method and program according to the present technology by the computer system includes both the case where the generation of control information and the judgment on the necessity of the outer shape change are executed by a single computer and the case where respective processing are executed by different computers, for example. Further, the execution of the respective processing by a predetermined computer includes causing another computer to execute a part or all of the processing and acquiring results thereof. For example, the generation of control information by a computer A includes outputting notification information and the information related to the usage state to another computer B, for example, and receiving control information generated by the computer B.

In other words, the information processing method and program according to the present technology are also applicable to a configuration of cloud computing in which one function is shared and cooperatively processed by a plurality of apparatuses via a network.

In a case where the outer shape of the mobile apparatus that the user is capable of carrying is changeable and the notification is necessary, the outer shape of the mobile apparatus may be changed. For example, the notification may be made to the user by bending the outer shape of the mobile apparatus including a flexible substrate, a flexible display, and the like. Even in such a case, the effects described above can be exerted.

At least two of the feature portions according to the present technology described above can be combined. In other words, various feature portions described in the respective embodiments may be arbitrarily combined without distinguishing the embodiments from one another. Moreover, the various effects described above are mere examples and should not be limited thereto, and other effects may also be exerted.

It should be noted that the present technology can also take the following configurations.

(1) An information processing apparatus, including:
an acquisition unit that acquires information related to a notification to a user; and
a generation unit that generates control information for changing an outer shape of a wearable device on a basis of the information.

(2) The information processing apparatus according to (1), in which
the generation unit generates control information for changing the outer shape of the wearable device into a shape corresponding to the information.

(3) The information processing apparatus according to (2), further including
a judgment unit that judges whether to change the outer shape of the wearable device on the basis of the information.

(4) The information processing apparatus according to (2) or (3), in which
the generation unit generates the control information on a basis of detection information detected by a sensor provided in the wearable device.

(5) The information processing apparatus according to (4), in which
the sensor includes a biological sensor, and
the detection information includes biological information detected by the biological sensor.

(6) The information processing apparatus according to (5), further including
a judgment unit that judges whether to change the outer shape of the wearable device on the basis of the detection information.

(7) The information processing apparatus according to any one of (2) to (6), in which
the information includes a notification related to a predetermined service, a notification related to an apparatus state of the information processing apparatus, or a notification related to biological information of the user.

(8) The information processing apparatus according to any one of (2) to (7), in which
the control information includes a mode of the change of the outer shape into the shape corresponding to the information.

(9) The information processing apparatus according to any one of (2) to (8), in which
the generation unit generates, in a case of canceling the notification to the user, cancel control information for changing the outer shape into a predetermined shape from the shape corresponding to the information.

(10) The information processing apparatus according to (9), in which
the predetermined shape is the outer shape of the wearable device in a basic state.

(11) The information processing apparatus according to any one of (2) to (10), in which
the information processing apparatus is integrated with the wearable device, and
the wearable device includes a holding function for holding the outer shape in the shape corresponding to the information.

(12) The information processing apparatus according to any one of (2) to (11), further including
a judgment unit that judges whether to change the outer shape of the wearable device on a basis of information related to a usage state of the information processing apparatus.

(13) The information processing apparatus according to any one of (2) to (12), in which
the generation unit sets the shape corresponding to the information on a basis of information related to a usage state of the information processing apparatus.
(14) The information processing apparatus according to any one of (1) to (13), in which
the generation unit generates the control information for changing at least a part of a portion of the wearable device that comes into contact with the user.
(15) The information processing apparatus according to any one of (1) to (14), further including
a judgment unit that judges that it is necessary to change the outer shape of the wearable device in a case where a predetermined movement is made by the user wearing the wearable device.
(16) The information processing apparatus according to any one of (1) to (15), further including
an execution unit that executes predetermined processing in a case where the user changes the outer shape into another shape from the shape corresponding to the information.
(17) A wearable apparatus, including:
a contact portion that comes into contact with a user;
a driving mechanism that causes an outer shape of the contact portion to be changed;
an acquisition unit that acquires information related to a notification to the user; and
an output unit that generates control information for changing the outer shape of the contact portion and outputs the control information to the driving mechanism.

REFERENCE SIGNS LIST

F0 outer shape in basic state
1 user
10 computer main body
11 controller
20 sensor unit
23 notification information table
30 band unit
31 attachment band
32 driving unit
33 drive unit
34 shape sensor
35 plastic deformation member
36 first shape-memory alloy (SMA)
37 second shape-memory alloy (SMA)
38a first joint portion
38b second joint portion
39 wire
41 acquisition unit
42 generation unit
43 judgment unit
50 inflation member
52 joint portion
53 lock mechanism
54 string
100 wearable apparatus
110 wristband-type apparatus
120 bracelet-type apparatus
130 headband-type (head-mounted type) apparatus
140 neckband-type apparatus
150 apparatus for body
160 belt-type apparatus
170 anklet-type apparatus

The invention claimed is:

1. An information processing apparatus, comprising:
an acquisition unit configured to acquire notification information to be notified to a user, wherein the acquired notification information includes biological information of the user; and
a generation unit configured to:
generate control information to change an outer shape of a wearable device from a first shape to a second shape, wherein
the control information is generated based on the biological information of the user, and
the change of the outer shape of the wearable device from the first shape to the second shape corresponds to the notification of the acquired notification information; and
generate cancel control information to change the outer shape of the wearable device from the second shape to a third shape, wherein
the first shape, the second shape, and the third shape are different from each other, and
the cancel control information is generated based on an input that indicates the notification of the acquired notification information has been checked by the user.

2. The information processing apparatus according to claim 1, further comprising a judgment unit configured to judge whether to change the outer shape of the wearable device from the first shape to the second shape, wherein the judgement is based on the acquired notification information.

3. The information processing apparatus according to claim 1, wherein
the wearable device includes a sensor, and
the generation unit is further configured to generate the control information based on detection information detected by the sensor.

4. The information processing apparatus according to claim 3, wherein
the sensor includes a biological sensor, and
the detection information includes the biological information detected by the biological sensor.

5. The information processing apparatus according to claim 4, further comprising a judgment unit configured to judge whether to change the outer shape of the wearable device from the first shape to the second shape,
wherein the judgement is based on the detection information.

6. The information processing apparatus according to claim 1, wherein the acquired notification information includes at least one of a notification related to a specific service or a notification related to an apparatus state of the information processing apparatus.

7. The information processing apparatus according to claim 1, wherein
the control information includes a mode of the change of the outer shape from the first shape to the second shape, and
the mode corresponds to the acquired notification information.

8. The information processing apparatus according to claim 1, wherein
the generation unit is further configured to generate the cancel control information based on cancelation of the notification of the acquired notification information.

9. The information processing apparatus according to claim 1, wherein the first shape is the outer shape of the wearable device in a basic state.

10. The information processing apparatus according to claim 1, wherein
the information processing apparatus is integrated with the wearable device, and
the wearable device includes a holding function to hold the outer shape in the second shape.

11. The information processing apparatus according to claim 1, further comprising a judgment unit configured to judge whether to change the outer shape of the wearable device from the first shape to the second shape,
wherein the judgement is based on information related to a usage state of the information processing apparatus.

12. The information processing apparatus according to claim 1, wherein the generation unit is further configured to set the second shape based on information related to a usage state of the information processing apparatus.

13. The information processing apparatus according to claim 1, wherein
the generation unit is further configured to generate the control information to change at least a part of a portion of the wearable device, and
the at least the part of the portion of the wearable device is in contact with the user.

14. The information processing apparatus according to claim 1, further comprising a judgment unit configured to judge a necessity to change the outer shape of the wearable device from the first shape to the second shape,
wherein the judgement is based on a specific movement of the wearable device.

15. The information processing apparatus according to claim 1, further comprising an execution unit configured to execute a specific process based on the change of the outer shape of the wearable device from the second shape to the third shape by the user.

* * * * *